(12) United States Patent
Dotson et al.

(10) Patent No.: US 6,599,971 B2
(45) Date of Patent: Jul. 29, 2003

(54) METALS SALTS OF HEXAHYDROPHTHALIC ACID AS NUCLEATING ADDITIVES FOR CRYSTALLINE THERMOPLASTICS

(75) Inventors: Darin L. Dotson, Spartanburg, SC (US); X. Edward Zhao, Moore, SC (US)

(73) Assignee: Milliken & Company, Spartanburg, SC (US)

( * ) Notice: Subject to any disclaimer, the term of this patent is extended or adjusted under 35 U.S.C. 154(b) by 37 days.

(21) Appl. No.: 09/820,569

(22) Filed: Mar. 29, 2001

(65) Prior Publication Data

US 2003/0027908 A1 Feb. 6, 2003

(51) Int. Cl.[7] .............................. C08K 5/04; C08K 5/09; C07C 69/74
(52) U.S. Cl. ..................... 524/394; 560/116; 560/117; 560/118; 560/125; 560/126; 560/127
(58) Field of Search .................. 524/394; 560/116, 560/117, 118, 125, 126, 127

(56) References Cited

U.S. PATENT DOCUMENTS

| | | | | |
|---|---|---|---|---|
| 3,207,735 A | * | 9/1965 | Wijga | 542/111 |
| 3,207,736 A | * | 9/1965 | Wijga | 524/295 |
| 3,207,737 A | * | 9/1965 | Wales | 524/396 |
| 3,207,738 A | * | 9/1965 | Wijga | 524/285 |
| 3,207,739 A | * | 9/1965 | Wales | 524/396 |

OTHER PUBLICATIONS

Beck, H.N., "Heterogenous Nucleating Agents for Polypropylene Crystallization", Journal of Applied Polymer Science, vol. 11, pp. 673–685 (1967).*

* cited by examiner

*Primary Examiner*—Kriellion A. Sanders
(74) *Attorney, Agent, or Firm*—Terry T. Moyer; William S. Parks

(57) ABSTRACT

Compounds and compositions comprising specific metal salts of hexahydrophthalic acid (HHPA) in order to provide highly desirable properties within thermoplastic articles are provided. The inventive HHPA derivatives are useful as nucleating and/or clarifying agents for such thermoplastics, are practical and easy to handle. Such compounds provide excellent crystallization temperatures, stiffness, and acid scavenger compatibility within target polyolefins. Also, such compounds exhibit very low hygroscopicity and therefore excellent shelf stability as powdered or granular formulations. Thermoplastic additive compositions and methods of producing polymers with such compounds are also contemplated within this invention.

15 Claims, No Drawings

# METALS SALTS OF HEXAHYDROPHTHALIC ACID AS NUCLEATING ADDITIVES FOR CRYSTALLINE THERMOPLASTICS

FIELD OF THE INVENTION

This invention relates to compounds and compositions comprising specific metal salts of hexahydrophthalic acid (hereinafter HHPA) in order to provide highly desirable properties within thermoplastic articles. The inventive HHPA derivatives are useful as nucleating and/or clarifying agents for such thermoplastics, and are practical to produce and handle. Such compounds provide excellent crystallization temperatures, stiffness, and acid scavenger compatibility within target polyolefins. Also, such compounds exhibit very low hygroscopicity and therefore excellent shelf stability as powdered or granular formulations. Thermoplastic additive compositions and methods of producing polymers with such compounds are also contemplated within this invention.

BACKGROUND OF THE PRIOR ART

All U.S. patents cited below are herein fully incorporated by reference.

As used herein, the term "thermoplastic" is intended to mean a polymeric material that will melt upon exposure to sufficient heat but will retain its solidified state, but not prior shape without use of a mold or like article, upon sufficient cooling. Specifically, as well, such a term is intended solely to encompass polymers meeting such a broad definition that also exhibit either crystalline or semi-crystalline morphology upon cooling after melt-formation. Particular types of polymers contemplated within such a definition include, without limitation, polyolefins (such as polyethylene, polypropylene, polybutylene, and any combination thereof), polyamides (such as nylon), polyurethanes, polyesters (such as polyethylene terephthalate), and the like (as well as any combinations thereof).

Thermoplastics have been utilized in a variety of end-use applications, including storage containers, medical devices, food packages, plastic tubes and pipes, shelving units, and the like. Such base compositions, however, must exhibit certain physical characteristics in order to permit widespread use. Specifically within polyolefins, for example, uniformity in arrangement of crystals upon crystallization is a necessity to provide an effective, durable, and versatile polyolefin article. In order to achieve such desirable physical properties, it has been known that certain compounds and compositions provide nucleation sites for polyolefin crystal growth during molding or fabrication. Generally, compositions containing such nucleating compounds crystallize at a much faster rate than unnucleated polyolefin. Such crystallization at higher temperatures results in reduced fabrication cycle times and a variety of improvements in physical properties, such as, as one example, stiffness.

Such compounds and compositions that provide faster and/or higher polymer crystallization temperatures are thus popularly known as nucleators. Such compounds are, as their name suggests, utilized to provide nucleation sites for crystal growth during cooling of a thermoplastic molten formulation. Generally, the presence of such nucleation sites results in a larger number of smaller crystals. As a result of the smaller crystals formed therein, clarification of the target thermoplastic may also be achieved, although excellent clarity is not always a result. The more uniform, and preferably smaller, the crystal size, the less light is scattered. In such a manner, the clarity of the thermoplastic article itself can be improved. Thus, thermoplastic nucleator compounds are very important to the thermoplastic industry in order to provide enhanced clarity, physical properties and/or faster processing.

As an example, dibenzylidene sorbitol derivatives are common nucleator compounds, particularly for polypropylene end-products. Compounds such as 1,3-O-2,4-bis(3,4-dimethylbenzylidene) sorbitol (hereinafter DMDBS), available from Milliken Chemical under the trade name Millad® 3988, provide excellent nucleation and clarification characteristics for target polypropylenes and other polyolefins. Other well known nucleator compounds include sodium benzoate, sodium 2,2'-methylene-bis-(4,6-di-tert-butylphenyl) phosphate (from Asahi Denka Kogyo K.K., known as NA-11), aluminum bis[2,2'-methylene-bis-(4,6-di-tert-butylphenyl)phosphate] (also from Asahi Denka Kogyo K.K., known as NA-21), talc, and the like. Such compounds all impart high polyolefin crystallization temperatures; however, each also exhibits its own drawback for large-scale industrial applications.

For example, of great interest is the compatibility of such compounds with different additives widely used within typical polyolefin (e.g., polypropylene, polyethylene, and the like) plastic articles. For instance, calcium stearate is a very popular acid neutralizer present within typical polypropylene formulations to protect the stabilizing additives (such as light stabilizers, antioxidants, etc.) from catalyst residue attack. Unfortunately, most of the nucleator compounds noted above also exhibit deleterious reactions with calcium stearate within polyolefin articles. For sodium, and other like metal ions, it appears that the calcium ion from the stearate transfers positions with the sodium ions of the nucleating agents, rendering the nucleating agents ineffective for their intended function. As a result, such compounds sometimes exhibit unwanted plate-out characteristics and overall reduced nucleation performance (as measured, for example, by a decrease in crystallization temperature during and after polyolefin processing). Other processing problems are evident with such compounds as well.

Other problems encountered with the standard nucleators noted above include inconsistent nucleation due to dispersion problems, resulting in stiffness and impact variation in the polyolefin article. Substantial uniformity in polyolefin production is highly desirable because it results in relatively uniform finished polyolefin articles. If the resultant article does not contain a well-dispersed nucleating agent, the entire article itself may suffer from a lack of rigidity and low impact strength.

Furthermore, storage stability of nucleator compounds and compositions is another potential problem with thermoplastic nucleators and thus is of enormous importance as well. Since nucleator compounds are generally provided in powder or granular form to the polyolefin manufacturer, and since uniform small particles of nucleating agents is imperative to provide the requisite uniform dispersion and performance, such compounds must remain as small particles through storage. Certain nucleators, such as sodium benzoate, exhibit high degrees of hygroscopicity such that the powders made therefrom hydrate easily resulting in particulate agglomeration. Such agglomerated particles may require further milling or other processing for deagglomeration in order to achieve the desired uniform dispersion within the target thermoplastic. Furthermore, such unwanted agglomeration due to hydration may also cause feeding and/or handling problems for the user.

These noticeable problems have thus created a long-felt need in the thermoplastic industry to provide nucleating/clarifying agents that do not exhibit the aforementioned problems and provide excellent peak crystallization temperatures for the target thermoplastics themselves, particularly with a wide variety of typical and necessary acid scavenger additives. To date, the best compounds for this purpose remain those noted above. Unfortunately, nucleators exhibiting exceptionally high peak crystallization temperatures, low hygroscopicity properties, excellent dispersion and concomitant clarity and stiffness, as well as compatibility with most standard polyolefin additives (such as, most importantly, calcium organic salt acid scavengers) have not been accorded the different thermoplastic industries. Such problems are not limited to polyolefins and are common within all thermoplastic applications in which nucleating agents are used.

OBJECTS OF THE INVENTION

Therefore, an object of the invention is to provide a nucleator compound and compositions thereof that exhibit excellent calcium stearate compatibility within target thermoplastic articles and formulations. A further object of the invention is to provide a thermoplastic nucleating agent that provides excellent high peak crystallization temperatures, for example, to polypropylene articles and formulations, and also exhibits extremely low hygroscopicity in order to accord an extremely good shelf-stable additive composition. Another object of the invention is to provide an easily dispersed nucleator compound such that said polyolefin exhibits very high stiffness and good clarity. Additionally, it is an object of this invention to provide a nucleator compound or composition which may be used in various thermoplastic media for myriad end-uses.

Accordingly, this invention encompasses metal salts of a compound conforming to Formula (I)

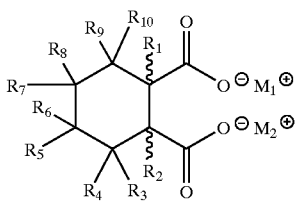

(I)

wherein $M_1$ and $M_2$ are the same or different and are selected from at least one metal cation of calcium, strontium, lithium, and monobasic aluminum, and wherein $R_1$, $R_2$, $R_3$, $R_4$, $R_5$, $R_6$, $R_7$, $R_8$, $R_9$, and $R_{10}$ are either the same or different and are individually selected from the group consisting of hydrogen, $C_1$–$C_9$ alkyl [wherein any two vicinal (neighboring) or geminal (same carbon) alkyl groups may be combined to form a carbocyclic ring of up to six carbon atoms], hydroxy, $C_1$–$C_9$ alkoxy, $C_1$–$C_9$ alkyleneoxy, amine, and $C_1$–$C_9$ alkylamine, halogens (fluorine, chlorine, bromine, and iodine), and phenyl. The term "monobasic aluminum" is well known and is intended to encompass an aluminum hydroxide group as a single cation bonded with the two carboxylic acid moieties. Furthermore, form each of these potential salts, the stereochemistry at the asymmetric carbon atoms may be cis or trans, although cis is preferred.

DETAILED DESCRIPTION OF THE INVENTION

As noted above, in order to develop a proper thermoplastic nucleator for industrial applications, a number of important criteria needed to be met. The inventive calcium, strontium, monobasic aluminum, and lithium HHPA salts meet all of these important requirements very well. For instance, these inventive compounds do not hydrate readily and thus granular or powder formulations of such a salt do not agglomerate or clump together. The cost benefits from such shelf stability are apparent since there is little if any need to separate agglomerated powders upon introduction to thermoplastic processing equipment. Furthermore, as discussed in greater detail below, these inventive salts provide excellent high peak crystallization temperatures in a variety of polyolefin and polyester formulations, particularly within random copolymer polypropylene (hereinafter RCP), homopolymer polypropylene (hereinafter HP), impact copolymer polypropylene (hereinafter ICP), syndiotactic polypropylene (s-PP), polyethylene terephthalate (hereinafter PET), polyamides (such as nylons), and any combinations thereof. Additionally, such inventive salts provide high stiffness (modulus) characteristics to the overall final polyolefin product without the need for extra fillers and reinforcing agents. Lastly, and of great importance within the polypropylene industry, such inventive salts do not react deleteriously with calcium stearate co-additives. Such a property, combined with the other attributes, is highly unexpected and unpredictable.

Such inventive compounds thus provide excellent nucleating capability. Sodium salts of certain aromatic and cycloaliphatic carboxylic acids have been discussed within the prior art, most notably within U.S. Pat. No. 3,207,739 to Wales. Broadly disclosed, the patentee includes metal salts of a number of such compounds, most particularly sodium, although Group I and II metals are also broadly discussed. However, patentee specifically states that aromatic benzoates, in particular sodium benzoate, are the best compounds for polyolefin nucleation purposes. Furthermore, patentee mentions strontium as a cation for benzoate alone and specifically teaches away from the utilization of calcium salts due to heat processing problems. Additionally, patentee equates Group I and II metals as cations for his preferred benzoates; however, as discussed below in greater detail, it is evident that other Group II metals, such as magnesium and barium, are highly ineffective with HHPA as polyolefin nucleators. Lastly, it has now been found that in comparison with patentee's decidedly preferred sodium benzoate, the inventive compounds provide more beneficial properties, including, without limitation, less susceptibility to plate-out and blooming on the mold during polyolefin article formation, lower hygroscopicity, and again of greater importance, less reactivity with calcium stearate thereby permitting greater amounts of both compounds to function in their intended capacities within the target polyolefin formulation.

The inventive HHPA salts are thus added within the target thermoplastic in an amount from about 0.01 percent to 2.0 percent by weight, more preferably from about 0.2 to about 1.5 percent, and most preferably from about 0.05 to 1.0 percent, in order to provide the aforementioned beneficial characteristics. It may also be desirable to include up to 50% or more of the active compound in a masterbatch, although this is not a restriction. Optional additives within the inventive HHPA salt-containing composition, or within the final thermoplastic article made therewith, may include plasticizers, stabilizers, ultraviolet absorbers, and other similar standard thermoplastic additives. Other additives may also be present within this composition, most notably antioxidants, antimicrobial agents (such as silver-based compounds, preferably ion-exchange compounds such as ALPHASAN® antimicrobials from Milliken & Company), antistatic compounds, perfumes, chlorine scavengers, and the like. These coadditives, along with the nucleating agents, may be present as an admixture in powder, liquid, or in compressed/pelletized form for easy feeding. The use of dispersing aids may be desirable, such as polyolefin (e.g., polyethylene) waxes, stearate esters of glycerin, montan waxes, and mineral oil. Basically, the inventive metal HHPA compounds may be present (up to 20% by weight or more) in any type of standard thermoplastic (e.g., polyolefin, most preferably) additive form, including, without limitation, powder, prill, agglomerate, liquid suspension, and the like, particularly comprising the dispersing aids described above. Compositions made from blending, agglomeration, compaction, and/or extrusion may also be desirable.

The term polyolefin or polyolefin resin is intended to encompass any materials comprised of at least one semicrystalline polyolefin. Preferred examples include isotactic and syndiotactic polypropylene, polyethylene, poly(4-methyl)pentene, polybutylene, and any blends or copolymers thereof, whether high or low density in composition. The polyolefin polymers of the present invention may include aliphatic polyolefins and copolymers made from at least one aliphatic olefin and one or more ethylenically unsaturated co-monomers. Generally, the co-monomers, if present, will be provided in a minor amount, e.g., about 10 percent or less or even about 5 percent or less, based upon the weight of the polyolefin. Such comonomers may serve to assist in clarity improvement of the polyolefin, or they may function to improve other properties of the polymer. Higher amounts of co-monomer (for instance, ethylene, e.g., 10–25% or more), may also be present in the polyolefin to engender greater impact resistance (hereinafter impact copolymer, or ICP's). Other polymers or rubber (such as EPDM or EPR) may also be compounded with the polyolefin. Other co-monomer examples include acrylic acid and vinyl acetate, etc. Examples of olefin polymers whose transparency and crystallization temperature can be improved conveniently according to the present invention are polymers and copolymers of aliphatic mono-olefins containing 2 to about 6 carbon atoms which have an average molecular weight of from about 10,000 to about 2,000,000, preferably from about 30,000 to about 300,000, such as, without limitation, polyethylene (PE), linear low density polyethylene (LLDPE), isotactic polypropylene (I-PP), syndiotactic polypropylene (s-PP), random copolymer polypropylene (RCP), crystalline ethylenepropylene copolymer (ICP), poly(1-butene), poly(4-methylpentene), poly(1-hexene), poly(1-octene), and poly(vinyl cyclohexene). The polyolefins of the present invention may be described as basically linear, regular polymers that may optionally contain side chains such as are found, for instance, in conventional, low density polyethylene. Although polyolefins are preferred, the nucleating agents of the present invention are not restricted to polyolefins, and may also give beneficial nucleation properties to polymers such as polyethylene terephthalate (PET), polybutylene terephthalate (PBT), and polyethylene naphthalate (PEN), as well as polyamides such as Nylon 6, Nylon 6,6, and others. Generally, any thermoplastic composition having some degree of crystalline content may be improved with the nucleating agents of the present invention.

The compositions of the present invention may be obtained by adding the inventive HHPA salt (or combination of salts or composition comprising such salts) to the thermoplastic polymer or copolymer and merely mixing the resultant composition by any suitable means. The composition may then be processed and fabricated by any number of different techniques, including, without limitation, injection molding, injection blow molding, injection stretch blow molding, injection rotational molding, extrusion, extrusion blow molding, sheet extrusion, film extrusion, cast film extrusion, foam extrusion, thermoforming (such as into films, blown-films, biaxially oriented films), thin wall injection molding, and the like into a fabricated article.

The nucleated thermoplastic is intended to be utilized as, for instance and not by limitation, medical devices, such as pre-filled syringes for retort applications, intravenous supply containers, and blood collection apparati; food packages; liquid containers, such as for drinks, medicines, shampoos, and the like; apparel cases; microwaveable articles; shelves; cabinet doors; mechanical parts; automobile parts; sheet; pipes and tubes; rotationally molded products; blow-molded products; fiber (spun or nonwoven); compression molded products; basically any thermoplastic article wherein the effects of nucleation may be advantageous.

Preferred Embodiments of the Invention

Examples of the particularly preferred metal salts of HHPA within the scope of the present invention and compositions thereof are presented below.

Production of Inventive HHPA Salts

EXAMPLE 1

Cis-Calcium HHPA:

To an 8-L cylindrical kettle fitted with a mechanical paddle stirrer and thermometer was added water (4 L) and calcium hydroxide (481 g, 6.49 moles) with stirring at room temperature. To this slurry was added cis-hexahydrophthalic anhydride (1 kg, 6.49 moles) and the slurry was heated to 50° C. After stirring with heat for 5 hours, the mixture became quite thick, at which time the pH of the aqueous phase was found to be about 7. The white product was collected by suction filtration, washed with copious amounts of water, and dried in a vacuum oven overnight at 140° C. The dry weight was 1270 grams (93% yield) having a melting point greater than about 400° C. The IR and NMR spectra were consistent with the expected product.

EXAMPLE 2

Cis-Strontium HHPA:

To an 500-mL round bottom flask with a mechanical stirrer and reflux condenser was added cis-hexahydrophthalic anhydride (15.4 g, 100 mmol), water (200 mL), and sodium hydroxide (16 g, 400 mmol) and the mixture heated to 50° C. After stirring with heat for 2 hours, a solution of strontium chloride hexahydrate (26.7 g, 168 mmol) was added and a white flocculate appeared immediately. The white product was collected by suction filtration, washed with copious amounts of water, and dried in a vacuum oven overnight at 110° C. The dry weight was 25 grams (97% yield) with a melting point in excess of about 400° C. The IR and NMR spectra were consistent with the expected product.

EXAMPLE 3

Cis-Dilithium HHPA

To a 1-L 3-necked round bottom flask fitted with a reflux condenser, mechanical stirrer, and thermometer was added water (300 mL), lithium hydroxide monohydrate (17.7 g, 421 mmol), and cis-hexahydrophthalic anhydride (30.8 g, 200 mmol). After heating at reflux for 3 hours, the reaction mixture was cooled and then poured into acetone (500 mL). No precipitate formed, and the solvents were removed by rotary evaporation to give a white powder. The powder was washed on a filter with 50 mL of cold water, and the solid was dried in a vacuum oven at 85° C. overnight. The dry weight as about 37 grams (100%), with a melting point greater than about 350° C. IR and NMR analysis were consistent with that of the expected product.

EXAMPLE 4
Cis-Monobasic Aluminum HHPA

To a 500-mL round bottom flask with a mechanical stirrer was added cis-disodium HHPA (10 g, 46.2 mmol) and water (100 mL). When homogeneity was obtained, a solution of aluminum sulfate (15.4 g, 23 mmol) in water (100 mL) was added, at which time a white flocculate formed immediately. After stirring at 50° C. for 30 minutes, the pH was adjusted to 9, the white solid was collected via suction filtration, washed with water (200 mL), and dried in a vacuum oven overnight at 100° C. The dry weight equaled 8.7 grams (88%) with a melting point of greater than about 400° C. IR and NMR analysis were consistent with that of the expected structure.

EXAMPLE 5 (Comparative)
Cis-Magnesium HHPA

To a 500-mL Erlenmeyer flask with a magnetic stirring bar was added water (200 mL) and cis-disodium HHPA (20 g, 92.4 mmol) with stirring. After homogeneity was obtained, a solution of magnesium sulfate (11.1 g, 92.4 mmol) in water (100 mL) was slowly added. After stirring for 3 hours, the solvent was removed by rotary evaporation, affording a white solid. The sodium sulfate by-product was removed by sonicating the powder in methanol (300 mL), filtering, and drying in a vacuum oven at 110° C. overnight. Dry weight=17 grams (95%), mp>400° C. IR and NMR analysis were consistent with that of the expected product.

EXAMPLE 6 (Comparative)
Cis-Barium HHPA

To a 500-mL round bottom flask with a mechanical stirrer was added cis-hexahydrophthalic anhydride (15.4 g, 100 mmol), water (200 mL), and sodium hydroxide (16 g, 400 mmol). When homogeneity was obtained, a solution of barium chloride (20.8 g, 100 mmol) in water (50 mL) was added, at which time a white flocculate formed immediately. After stirring for 30 minutes, the white solid was collected via suction filtration, washed with water (100 mL), and dried in a vacuum oven overnight at 115° C. Dry weight=30.7 grams (99%), mp>400° C. IR and NMR analysis were consistent with that of the expected structure.

EXAMPLE 7 (Comparative)
Cis-Disilver HHPA

To a 500-mL round bottom flask with a mechanical stirrer was added cis-disodium HHPA (20 g, 92.4 mmol) and water (100 mL). When homogeneity was obtained, a solution of silver nitrate (31.39 g, 184.8 mmol) in water (100 mL) was added, at which time a white flocculate formed immediately. After stirring for 30 minutes, the white solid was collected via suction filtration, washed with water (200 mL), and dried in a vacuum oven overnight at 110° C. Dry weight=27.8 grams (78%), mp>400° C. IR and NMR analysis were consistent with that of the expected structure.

EXAMPLE 8 (Comparative)
Cis-Dipotassium HHPA

To a 500-mL round bottom flask with a stir bar and reflux condenser was added cis-hexahydrophthalic anhydride (44 g, 285.4 mmol), water (200 mL), and potassium hydroxide (32 g, 570.8 mmol). When homogeneity was obtained, the solution was heated at reflux for 2 hours. The solution was cooled, and the solvent removed via rotary evaporation. The white solid was washed with acetone (250 mL), filtered and dried in a vacuum oven overnight at 100° C. Dry weight= 59.8 grams (84%), mp>400° C. IR and NMR analysis were consistent with that of the expected structure. The sample proved to be too hygroscopic for testing in plastic (see Table 3 for hygroscopicity results).

Production of Nucleated Polyolefins with Inventive HHPA Salts

Before molding into polypropylene plaques, one kilogram batches of target polypropylene pellets were produced in accordance with the following table:

| HOMOPOLYMER POLYPROPYLENE COMPOSITION TABLE | |
|---|---|
| Component | Amount |
| Polypropylene homopolymer (Himont Profax ® 6301) | 1000 g |
| Irganox ® 1010, Primary Antioxidant (from Ciba) | 500 ppm |
| Irgafos ® 168, Secondary Antioxidant (from Ciba) | 1000 ppm |
| Acid Scavenger (either Calcium Stearate, Lithium Stearate or DHT4-A) | as noted |
| Inventive HHPA salts | as noted |

The base resin (polypropylene homopolymer, hereinafter "HP") and all additives were weighed and then blended in a Welex mixer for 1 minute at about 1600 rpm. All samples were then melt compounded on a Killion single screw extruder at a ramped temperature from about 204° to 232° C. through four heating zones. The melt temperature upon exit of the extruder die was about 246° C. The screw had a diameter of 2.54 cm and a length/diameter ratio of 24:1. Upon melting the molten polymer was filtered through a 60 mesh (250 micron) screen. Plaques of the target polypropylene were then made through extrusion into an Arburg 25 ton injection molder. The molder was set at a temperature anywhere between 190 and 260° C., with a range of 190 to 240° C. preferred, most preferably from about 200 to 230° C. (for the Tables below, the standard temperature was 220° C.). The plaques had dimensions of about 51 mm×76 mm×1.27 mm, and due to the mold exhibiting a mirror finish the resultant plaques exhibited a mirror finish as well. The mold cooling circulating water was controlled at a temperature of about 25° C. The same basic procedures were followed for the production of plaques of impact copolymer polypropylene (ICP, Table 2).

Flexural modulus testing (reported as 1% Secant Modulus) was performed on the above mentioned plaques using an MTS Sintech 1/S: 40" instrument with a span of 49 mm, a fixed deflection rate of 1.28 mm/min, a nominal sample thickness of 1.27 mm, and a nominal sample width of 50 mm in conformance with ASTM D790.

Nucleation capabilities were measured as polymer recrystallization temperatures (which indicate the rate of polymer crystal formation provided by the presence of the nucleating additive) by melting the target plaques, cooling the plaques at a rate of about 20° C./minute, and recording the temperature at which polymer crystal reformation occurs (Tc). Crystallization half-time (T½) is also a useful parameter which can determine to what extent a nucleating agent might reduce molding cycle times. In this test, the target plaques (ICP) were melted at 220° C., then quenched at a nominal rate of 200° C./min to 140° C., at which time the crystallization temperature at half height was measured. Control plaques without nucleating additives, as well as with NA-11 and NA-21 (from Asahi Denka) and sodium benzoate were also produced for comparative purposes for some or all of the above-noted measurements.

Tables 1 and 2 below show the performance data of several inventive HHPA salts in terms of peak crystallization temperature ($T_c$), percent haze, and flexural modulus (all temperatures listed below have a statistical error of +/−0.5° C., and all haze measurements have a statistical error of +/−0.25 haze units), and crystallization half-time (T½). The acid scavengers added were as follows: calcium stearate (CS), dihydrotalcite (commercial product from Kyowa Chemical known as DHT4-A), and lithium stearate (LS); such compounds were added in amounts of about 400–800 ppm within the target polypropylene compositions for formation of the test plaques, while the inventive HHPA salts were added at a concentration of 0.25% by weight unless otherwise noted. An asterisk (*) indicates no measurements were taken.

EXPERIMENTAL TABLE 1
Nucleation Performance of Inventive Salts in Homopolymer Polypropylene

| Plaque # | Nucleator Added (Ex. # from above) | Acid Scavenger Added | $T_c$ (° C.) | Haze (%) | 1% Secant Modulus, MPa (std. Dev.) |
|---|---|---|---|---|---|
| 10 | 1 | CS^ | 121 | 38 | 2209 (16.6) |
| 11 | 1 | DHT4-A^ | 122 | 53 | 2077 (8.3) |
| 12 | 1 | LS^ | 121 | 38 | 2190 (37.5) |
| 13 | 2 | CS | 120 | 43 | 2129 (17.9) |
| 14 | 2 | DHT4-A | 122 | 51 | 2060 (15.7) |
| 15 | 2 | LS | 120 | 37 | 2209 (3.3) |
| 16 | 3 | DHT4-A | 121 | 65 | 2023 (1.3) |
| 17 | 3 | LS | 121 | 61 | 1997 (25) |
| 18 (Comparatives) | 4 | LS | 121 | 56 | 2022 (6.9) |
| 19 | 5 | DHT4-A | 117 | 55 | 2026 (23.4) |
| 20 | 5 | LS | 114 | 67 | 1952 (18.3) |
| 21 | 6 | DHT4-A | 116 | 99 | 1892 (3.7) |
| 22 | 6 | CS | 115 | 78 | 1926 (4.2) |
| 23 | 7 | DHT4-A | 119 | 58 | * |
| 24 | Sodium Benzoate | None | 120 | 60 | * |
| 25 | Sodium Benzoate | CS | 116 | 62 | * |
| 26 (control) | None | CS | 112 | 64 | 1691 (18) |

^CS = Calcium Stearate at 800 ppm, LS = Lithium Stearate at 800 ppm, DHT4-A = Dihydrotalcite at 400 ppm.

Thus, the inventive HHPA salts exhibited more consistently high peak crystallization temperatures, as well as lower haze and more consistent high flexural modulus measurements than the comparative examples, particularly upon the introduction of highly desirable acid scavengers.

EXPERIMENTAL TABLE 2
Crystallization Half-Time of Example 1 vs. Comparative Examples in ICP

| Plaque # | Additives | Additive Concentration (ppm) | Cryst. Temp (DSC peak max.) | Crystallization Half-time (minutes) |
|---|---|---|---|---|
| 27 (comparative) | Control (None) | — | 115 | — |
| 28 | Example 1 | 2500 | 123 | 4.81 |
| 29 (comparative) | DMDBS | 2500 | 126 | 2.83 |
| 30 (comparative) | NA-11 | 1000 | 126 | 2.52 |
| 31 (comparative) | Sodium Benzoate | 2500 | 123 | 8.05 |
| 32 (comparative) | NA-21 | 2200 | 123 | 10.44 |

Thus, the inventive calcium HHPA salt exhibited acceptable peak crystallization temperatures and crystallization half-time measurements as compared the prior art nucleators.

Hygroscopicity Testing

These tests were carried out on the milled products to give adequate surface area for moisture uptake. Two grams of each example were spread out on a watch glass and weighed immediately after drying in a vacuum oven. The samples were then placed in a controlled humidity (65%) environment and the weight was taken each day for 7 days. The percent weight gain was defined as the percent moisture uptake at 7 days. Table 3 below summarizes the results:

EXPERIMENTAL TABLE 3
Hygroscopicity of Compounds

| Example # | % Water Absorbed |
|---|---|
| 1 | 0.20 |
| sodium benzoate (Comparative) | 1.20 |
| 8 (Comparative) | 38.00 |

It is clear from the above data that the inventive compound from Example 1 exhibits greatly reduced hygroscopicity over that of the prior art as well as a higher molecular weight Group I metal salt (dipotassium).

Production of Nucleated PET with Example 1 (5000 ppm)

Additives were compounded with a C. W. Brabender Torque Rheometer at 5000 ppm into Shell Cleartuff™ 8006 PET bottle grade resin having an IV of 0.80. All resin was dried to less than 20 ppm water. Samples were taken, pressed, and rapidly cooled into 20–40 mil films. All samples were dried at 150° C. under vacuum for 6 h prior to analysis. 5 mg samples were analyzed under nitrogen on a Perkin Elmer System 7 differential scanning calorimeter using a heating and cooling rate of 20° C./min. $T_c$ data was collected after holding the samples at 290° C. for 2 min. before cooling. The data is shown below in Table 4:

EXPERIMENTAL TABLE 4
Polymer Crystallization Temperature of Example 1 in PET

| Sample | $T_c$(° C.) |
|---|---|
| Control | 155 |
| Example 1 | 180 |

Thus, the inventive compound of Example 1 exhibited much improved nucleation of polyester over the control with no nucleator compound.

Having described the invention in detail it is obvious that one skilled in the art will be able to make variations and modifications thereto without departing from the scope of the present invention. Accordingly, the scope of the present invention should be determined only by the claims appended hereto.

That which is claimed is:

1. A metal salt of the compound conforming to Formula (I)

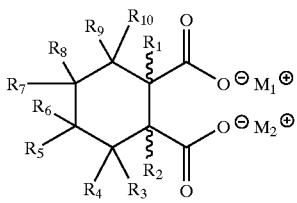

(I)

wherein $M_1$ and $M_2$ are combined to be a single cation selected from the group consisting of calcium and monobasic aluminum, and wherein $R_1$, $R_2$, $R_3$, $R_4$, $R_5$, $R_6$, $R_7$, $R_8$, $R_9$, and $R_{10}$ are either the same or different and are individually selected from the group consisting of hydrogen, $C_1$–$C_9$ alkyl, wherein any two vicinal or geminal alkyl groups may be combined to form a carbocyclic ring of up to six carbon atoms, hydroxy, $C_1$–$C_9$ alkoxy, $C_1$–$C_9$ alkyleneoxy, amine, and $C_1$–$C_9$ alkylamine, halogen, and phenyl.

2. The compound of claim 1 wherein each of $R_1$, $R_2$, $R_3$, $R_4$, $R_5$, $R_6$, $R_7$, $R_8$, $R_9$, and $R_{10}$ are hydrogen and $M_1$ and $M_2$ are combined as a single calcium ion.

3. The compound of claim 1 wherein each of $R_1$, $R_2$, $R_3$, $R_4$, $R_5$, $R_6$, $R_7$, $R_8$, $R_9$, and $R_{10}$ are hydrogen and $M_1$ and $M_2$ are combined as a single monobasic aluminum ion.

4. A polymer article comprising at least one thermoplastic component and at least one compound as defined in claim 1.

5. A polymer article comprising at least one thermoplastic component and at least one compound as defined in claim 2.

6. A polymer article comprising at least one thermoplastic component and at least one compound as defined in claim 5.

7. The thermoplastic polymer article of claim 4 wherein said polymer comprises polypropylene.

8. The thermoplastic polymer article of claim 5 wherein said polymer comprises polypropylene.

9. The thermoplastic polymer article of claim 6 wherein said polymer comprises polypropylene.

10. The thermoplastic polymer article of claim 4 wherein said polymer comprises polyester.

11. The thermoplastic polymer article of claim 5 wherein said polymer comprises polyester.

12. The thermoplastic polymer article of claim 6 wherein said polymer comprises polyester.

13. A polymer additive composition comprising at least one compound defined in claim 1, wherein said additive composition is present in a form selected from the group consisting of a powder, a pellet, or a liquid, and wherein said composition also comprises at least one thermoplastic polymer, and, optionally, at least one compound selected from the group consisting of plasticizers, acid scavengers, antioxidants, antimicrobials, flame retardants, light stabilizers, antistatic agents, blowing agents, colored pigments, and any combination thereof.

14. A polymer additive composition comprising at least one compound defined in claim 2, wherein said additive composition is present in a form selected from the group consisting of a powder, a pellet, or a liquid, and wherein said composition also comprises at least one thermoplastic polymer, and, optionally, at least one compound selected from the group consisting of plasticizers, acid scavengers, antioxidants, antimicrobials, flame retardants, light stabilizers, antistatic agents, blowing agents, colored pigments, and any combination thereof.

15. A polymer additive composition comprising at least one compound defined in claim 3, wherein said additive composition is present in a form selected from the group consisting of a powder, a pellet, or a liquid, and wherein said composition also comprises at least one thermoplastic polymer, and, optionally, at least one compound selected from the group consisting of plasticizers, acid scavengers, antioxidants, antimicrobials, flame retardants, light stabilizers, antistatic agents, blowing agents, colored pigments, and any combination thereof.

* * * * *

UNITED STATES PATENT AND TRADEMARK OFFICE
CERTIFICATE OF CORRECTION

PATENT NO. : 6,599,971 B2
DATED : July 29, 2003
INVENTOR(S) : Darin L. Dotson and X. Edward Zhao It is certified that error appears in the above-identified patent and that said Letters Patent is hereby corrected as shown below:

Title page,
Item [54], Title, delete the word "METALS" and insert the word -- METAL --.

Signed and Sealed this

Twenty-eighth Day of June, 2005

JON W. DUDAS
*Director of the United States Patent and Trademark Office*